United States Patent
Shirotake

(10) Patent No.: US 11,019,817 B2
(45) Date of Patent: Jun. 1, 2021

(54) ANTIMICROBIAL AGENT AGAINST GERMS WHICH HAS EXCELLENT PLANT DISEASE CONTROL EFFECT

(71) Applicant: Shoichi Shirotake, Yokohama (JP)

(72) Inventor: Shoichi Shirotake, Kanagawa (JP)

(*) Notice: Subject to any disclaimer, the term of this patent is extended or adjusted under 35 U.S.C. 154(b) by 358 days.

(21) Appl. No.: 15/754,911

(22) PCT Filed: Aug. 25, 2015

(86) PCT No.: PCT/JP2015/073798
§ 371 (c)(1),
(2) Date: Aug. 7, 2018

(87) PCT Pub. No.: WO2017/033272
PCT Pub. Date: Mar. 2, 2017

(65) Prior Publication Data
US 2018/0343860 A1    Dec. 6, 2018

(51) Int. Cl.
| | |
|---|---|
| *A01N 37/44* | (2006.01) |
| *A01N 37/34* | (2006.01) |
| *A01N 25/10* | (2006.01) |
| *A61K 31/785* | (2006.01) |
| *A61K 45/06* | (2006.01) |
| *A61K 31/721* | (2006.01) |
| *A01N 43/16* | (2006.01) |

(52) U.S. Cl.
CPC .............. *A01N 37/44* (2013.01); *A01N 37/34* (2013.01); *A01N 43/16* (2013.01); *A61K 31/721* (2013.01); *A61K 31/785* (2013.01); *A61K 45/06* (2013.01)

(58) Field of Classification Search
None
See application file for complete search history.

(56) References Cited

U.S. PATENT DOCUMENTS

| | | |
|---|---|---|
| 2010/0285140 A1 | 11/2010 | Shirotake |
| 2014/0065222 A1* | 3/2014 | Shirotake .............. A61K 9/5138 424/489 |
| 2015/0004202 A1 | 1/2015 | Shirotake |

FOREIGN PATENT DOCUMENTS

| | | |
|---|---|---|
| JP | 2008013523 A | 1/2008 |
| JP | 2012517452 A | 8/2012 |
| JP | 2015157778 A | 9/2015 |
| WO | 2010091499 A | 2/2010 |
| WO | 2012133648 A1 | 10/2012 |
| WO | 2013108871 A1 | 7/2013 |

OTHER PUBLICATIONS

International Search Report in corresponding International Application No. PCT/JP2015/073798, dated Nov. 9, 2015 (4 pages).
Mccarron P.A. et al., International Journal of Pharmaceutics, vol. 340: 182-190 (2007).
Mccarron P.A. et al., Biomaterials, vol. 25: 2399-2407 (2004).
Shirotake, S. et al., Improvement in antibacterial, antimold, and antiviral properties in materials, vol. 15. No. 4, 2015, English language translation.
Shoichi Shirotake: "Atarashii Kokin Kijo o Yusuru Nano Polymer to Koseibusshitsu Taiseikin eno Oyo", Convertech, vol. 39, No. 2, Feb. 15, 2011 (Feb. 15, 2011), pp. 112-116.

* cited by examiner

*Primary Examiner* — Bethany P Barham
*Assistant Examiner* — Peter Anthopolos
(74) *Attorney, Agent, or Firm* — Edell, Shapiro & Finnan, LLC

(57) ABSTRACT

Disclosed is a novel antimicrobial means which is effective against various types of fungi including pathogenic true fungi and phytopathogenic filamentous fungi. An antimicrobial agent against fungi according to the present invention comprises, as an effective ingredient, cyanoacrylate polymer particles having an average particle diameter of less than 1000 nm, which particles contain at least one selected from the group consisting of amino acids, amino acid derivatives, oligomers and polymers thereof, saccharides and polysorbates, and contain no antimicrobial active ingredient effective against the fungi. The antimicrobial agent is particularly useful as a control agent against plant diseases caused by filamentous fungi.

Figure 1:
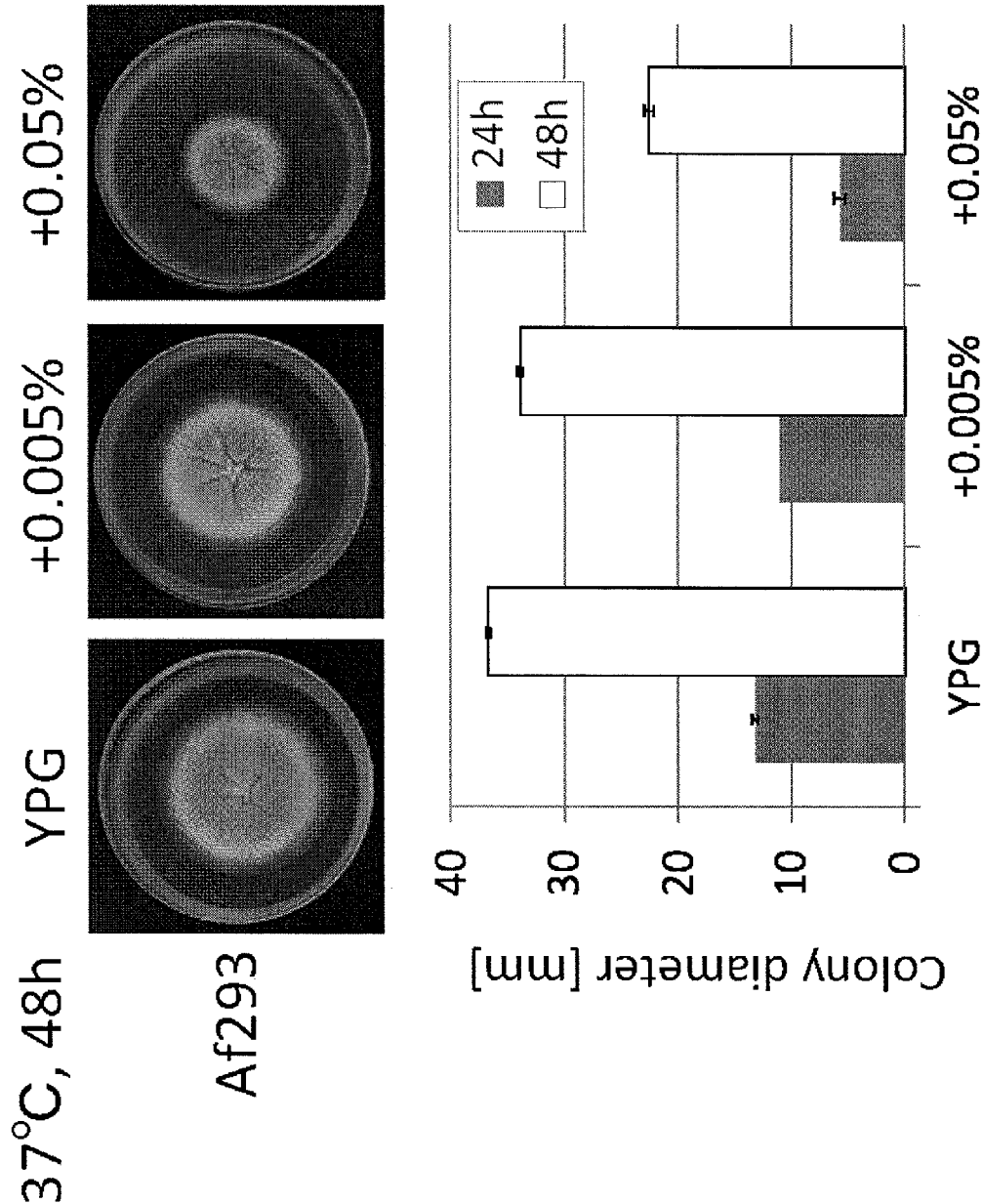

11 Claims, 8 Drawing Sheets

ANTIMICROBIAL AGENT AGAINST GERMS WHICH HAS EXCELLENT PLANT DISEASE CONTROL EFFECT

TECHNICAL FIELD

The present invention relates to an antimicrobial agent against fungi which comprises cyanoacrylate nanoparticles as an effective ingredient and has an excellent plant disease control effect.

BACKGROUND ART

Diseases of field and garden crops caused by pathogenic microorganisms such as filamentous fungi, bacteria and viruses are often growing into a serious issue in agriculture. Particularly, diseases caused by filamentous fungi account for about eighty percent of all plant diseases and are thus the most important targets in plant disease control. Although a variety of control agents against pathogenic microorganisms of various kinds have been developed, most of the agents with a high effect have a high impact on the environment. In addition, repeated use of the same kind of a control agent may render pathogenic microorganisms resistant to the agent, and use of such an agent is sometimes restricted. A control agent which has a lower toxicity to humans, livestock, fishes and birds, has a lower impact on the environment, and has a high effect, is always being demanded.

On the other hand, mainly aiming at application to pharmaceuticals for human, in order to improve the effect of pharmaceuticals by drug delivery system (DDS) or by sustained release, studies of nano-encapsulation of drugs are now under way. For example, DDS in which a drug is encapsulated in cyanoacrylate polymer particles is known (Patent Documents 1 and 2, and Non-Patent Document 1). The present inventor and co-workers also have disclosed a method for producing cyanoacrylate polymer particles with little irregularity in particle diameter, antibiotic-containing particles, and plasmid-containing particles (Patent Documents 3 to 5). In a conventional method for synthesizing polymer particles, a saccharide(s) and/or a polysorbate(s) is/are allowed to coexist with cyanoacrylate in a polymerization reaction system, for the purpose of triggering and stabilizing the anionic polymerization reaction. These past studies aimed at DDS or sustained release of drugs.

Thereafter, the present inventor found that cyanoacrylate polymer particles per se have an antibacterial activity against Gram-positive bacteria (Patent Document 6). Furthermore, the present inventor found that amino acid-containing cyanoacrylate polymer particles have an anticancer activity and also exert antibacterial activity against various types of bacteria, whether Gram-positive or Gram-negative (Patent Documents 7 to 9). Nano-sized polymer particles specifically adhere to the surface of bacteria to cause bacteriolysis. Cyanoacrylate nanoparticles exert their antibacterial activity by a mechanism completely different from those of antibiotics, and are effective even against multidrug-resistant bacteria such as MRSA and VRE.

However, the antimicrobial activity of cyanoacrylate nanoparticles against fungi has not been known.

PRIOR ART DOCUMENT(S)

Patent Document(s)

Patent Document 1: JP H11-503148 A
Patent Document 2: JP 2002-504526 A
Patent Document 3: JP 2008-127538 A
Patent Document 4: WO 2008/126846
Patent Document 5: JP 2008-208070 A
Patent Document 6: WO 2009/084494
Patent Document 7: WO 2010/101178
Patent Document 8: WO 2012/133648
Patent Document 9: WO 2013/108871

Non-Patent Document(S)

Non-Patent Document 1: Christine Vauthier et al., Adv. Drug Deliv. Rev., 55, 519-548 (2003)

SUMMARY OF THE INVENTION

Problems to be Solved by the Invention

An object of the present invention is to provide a novel antimicrobial means which is effective against various types of fungi including pathogenic true fungi and plant pathogenic filamentous fungi.

Means for Solving the Problems

The present inventor intensively studied and consequently found that nano-sized cyanoacrylate polymer particles can also exert antimicrobial effects on fungi, and thereby completed the present invention.

That is, the present invention provides an antimicrobial agent against fungi, comprising, as an effective ingredient, cyanoacrylate polymer particles having an average particle diameter of less than 1000 nm, which particles contain at least one selected from the group consisting of amino acids, amino acid derivatives, oligomers and polymers thereof, saccharides and polysorbates, and contain no antimicrobial active ingredient effective against the fungi.

Effect of the Invention

According to the present invention, a novel antimicrobial agent using cyanoacrylate nanoparticles to inhibit fungal growth was provided. The antimicrobial agent according to the present invention is a novel antimicrobial agent that is completely different from existing antibiotics, and therefore has no risk of creating new resistant microbes and is also available even in cases where new microbes resistant to existing antibiotics have emerged. Nanoparticles used in the present invention can be produced by the methods disclosed in Patent Documents 8 and 9, and the like, and it is known that nanoparticles produced by such a method do not harm normal mammalian cells and do not exhibit in vivo toxicity (see Patent Documents 8 and 9). Therefore, the antimicrobial agent according to the present invention has no risk of toxicity to humans, livestock, fishes and birds, as well as has a lower impact on the environment. Diseases caused by fungi often occur particularly in the agriculture and horticulture fields, and diseases caused by filamentous fungi account for about eighty percent of all plant diseases. The antimicrobial agent according to the present invention has a lower impact on the environment and is also very useful for the control of plant diseases caused by filamentous fungi. The nanoparticle-based antimicrobial agent according to the present invention can be used for the control of diseases caused by filamentous fungi in various field and garden crops, regardless of plant species. In addition, the nanoparticle-based antimicrobial agent according to the present invention can control diseases in field and garden crops with avoiding any damage to their commercial value and thus provide high-quality field and garden crops because the antimicrobial agent does not adversely affect the growth of plants.

BRIEF DESCRIPTION OF THE DRAWINGS

FIG. 1 shows the result of measuring the antimicrobial activity (inhibition of hyphal elongation) of Asp (aspartic acid)-containing nanoparticles against *Aspergillus fumigatus*. Representative images of cultures after incubation at 37° C. for 48 hours are shown in the upper panel. Measured values of colony diameter at 24 and 48 hours of incubation are shown in the lower panel.

FIG. 2 shows the result of measuring the antimicrobial activity (inhibition of hyphal elongation) of Asp-containing nanoparticles against *A. fumigatus, A. niger* and *A. oryzae*. Representative images of cultures after incubation at the indicated temperature for 48 hours are shown in left. Measured values of colony diameter at 48 hours of incubation are shown in the right graph.

FIG. 3 shows the result of measuring the antimicrobial activity (inhibition of spore germination) of Asp-containing nanoparticles against *A. fumigatus*. Germination was not observed in spores treated with the nanoparticles, even 7 hours after the treatment.

FIG. 4 shows the result of measuring the antimicrobial activity (inhibition of colony formation and growth) of Asp-containing nanoparticles against *Cryptococcus neoformans*. Representative images of cultures after incubation at 30° C. for 90 hours are shown in the upper panel. The graph in the lower panel shows the number of colonies detected at 90 hours of incubation.

FIG. 5 shows the result of measuring the antimicrobial activity (inhibition of hyphal elongation) of Asp-containing nanoparticles against *Fusarium oxysporum* and *Fusarium solani*. Representative images of cultures after incubation at 30° C. for 42 hours are shown.

FIG. 6 shows the result of measuring the antimicrobial activity (inhibition of hyphal elongation) of Asp-containing nanoparticles against *Magnaporthe oryzae* and *Alternaria alternata*. Representative images of cultures after incubation at 25° C. for 72 hours are shown.

FIG. 7 shows the result of measuring the antimicrobial activity (inhibition of hyphal elongation) of Asp-containing nanoparticles against *Botrytis cinerea*. Representative images of cultures after incubation at 25° C. for 48 hours are shown.

FIG. 8 shows pictures of fruits of a citrus variety, "Setoka", at six months after spraying an Asp-nanoparticle colloid solution in water on immature fruits.

MODE FOR CARRYING OUT THE INVENTION

An antimicrobial agent according to the present invention is an antimicrobial agent for use against fungi, and comprising nano-sized polymer particles (with an average particle diameter of less than 1000 nm) as an effective ingredient, which particles are obtained by anionic polymerization of cyanoacrylate monomer molecules. To initiate the anionic polymerization and stabilize the polymerization, in addition to a saccharide and a polysorbate, an amino acid, an amino acid derivative, an oligomer and polymer thereof (hereinafter, those are sometimes collectively referred to as "amino acid-based molecule") can be used. Any one of these polymerization initiators/stabilizers may be used alone, or two or more of these polymerization initiators/stabilizers may be used in combination. That is, the nanoparticles used in the present invention are particles containing at least one selected from the group consisting of amino acids, amino acid derivatives, oligomers and polymers thereof, saccharides, and polysorbates.

A method of producing nanoparticles in which a saccharide and/or a polysorbate is/are used as a polymerization initiator/stabilizer is known and described in Patent Document 3, Patent Document 4 (antibiotic-containing particles), Patent Document 5 (plasmid-containing particles), and the like. A method of producing nanoparticles in which an amino acid-based molecule is used as a polymerization initiator/stabilizer is known and described in Patent Documents 8 and 9 (use of an amino acid-based molecule alone), and the like. In addition, a production method for nanoparticles in which an amino acid is used in combination with a saccharide and/or a polysorbate is described in Patent Document 7.

In the present invention, the term "amino acid" refers to a compound which has an amino group(s) and a carboxy group(s) in the molecule, and as generally defined, the term also includes imino acids, which are cyclic secondary amine compounds in which a hydrogen of an amino group is substituted with another moiety in the molecule. Representative examples of the amino acid which may be used in the present invention include the 20 kinds of α-amino acids which constitute natural proteins, but the examples are not limited thereto and also include β-, γ- and δ-amino acid-based molecules. Specific examples thereof include, but are not limited to, arginine, histidine, lysine, aspartic acid, glutamic acid, alanine, glycine, leucine, valine, isoleucine, serine, threonine, phenylalanine, tryptophan, tyrosine, cystine or cysteine, glutamine, asparagine, proline, methionine, β-alanine, γ-aminobutyric acid (GABA; neurotransmitter), carnitine, γ-aminolevulinic acid, γ-aminovaleric acid, and the like.

The term "amino acid derivative" refers to a compound having a structure in which any of the groups in the amino acid as defined above is/are modified or substituted. Amino acid derivatives which naturally occur as biogenic substances may be usually preferably used in the present invention. Specific examples of the amino acid derivatives which may be used include, but are not limited to, creatine (an arginine derivative, 1-methylguanidinoacetic acid), ornithine (an arginine derivative, a product of urea cycle), thyroxine (triiodothyronine; T4, belonging to aromatic amino acids), desmosine (a component of comeum elastin and collagen; having a structure in which side chains of three allysine molecules are bound to a side chain of one lysine molecule), hydroxyproline and hydroxylysine (components of gelatin and collagen), phosphoserine (an ester of serine and phosphoric acid; a component of casein), theanine (a tee component, a glutamic acid derivative), kainic acid (an anthelmintic component from Digenea simplex), tricholomic acid (a component of Lyophyllum), sarcosine (a component of yolk, ham, legumes; N-methylglycine), and the like.

The term "amino acid oligomer" refers to an oligopeptide in which not more than 10 amino acid residues are linked by a peptide bond(s), and the term "amino acid polymer" refers to a polypeptide in which not less than 11 amino acid residues are linked by peptide bonds. Both may comprise not only an amino acid(s) but also an amino acid derivative(s) as residues. The upper limit of the number of residues in the polypeptide is not particularly limited, but the number of residues may be, for example, not more than 500. A polypeptide of 11-100 residues, 11-50 residues, 11-30 residues, 11-20 residues, or 11-15 residues may preferably be used.

An oligopeptide may be used more preferably than a polypeptide. In particular, an oligopeptide of 2-7 residues, 2-5 residues, or 2 or 3 residues may be more preferably used.

As described in the above-mentioned Patent Documents 8 and 9, nano-sized (less than 1000 nm) cyanoacrylate polymer particles can be synthesized by using any of the 20 kinds of α-amino acids which constitute natural proteins (i.e., arginine, histidine, lysine, aspartic acid, glutamic acid, alanine, glycine, leucine, valine, isoleucine, serine, threonine, phenylalanine, tryptophan, tyrosine, cystine or cysteine, glutamine, asparagine, proline, methionine) under conditions where neither a saccharide nor a polysorbate is used. It is demonstrated that nanoparticles can be produced by using any of neutral, acidic and basic amino acids, which may have any of linear, aromatic, imino, and sulfur-containing structures, without using either a saccharide or a polysorbate. Thus, not only the 20 kinds of α-amino acids, but also the above-described other amino acids and amino acid derivatives may be used in the synthesis of nanoparticles. In addition, oligopeptides and polypeptides may also be used in the synthesis of nanoparticles since they also have the amino acid structure in the molecule.

The term "saccharide" includes monosaccharides having a hydroxy group(s) (for example, glucose, mannose, ribose, fructose, and the like), disaccharides having a hydroxy group(s) (for example, maltose, trehalose, lactose, sucrose, and the like), and polysaccharides having a hydroxy group(s) (for example, dextran, mannan, and the like). These saccharides may be in either circular or linear form. Moreover, if those saccharides are circular, they may be in any of the pyranose type, the furanose type, and the like. In addition, saccharides have various isomers, and any of such isomers may be used in the present invention.

The term "polysorbate" includes various Tween-series surfactants such as polyoxyethylene sorbitan monolaurate (trade name: Tween 20), polyoxyethylene sorbitan monooleate (trade name: Tween 80), and the like.

Any one selected from monosaccharides, disaccharides, polysaccharides and polysorbates may be used alone, or two or more of them may be used in combination. Among the above-described saccharides and polysorbates, glucose, dextran, and Tween 20 (trade name) are inexpensively available and advantageous in terms of cost. As for the polymerization degree of dextran, dextran having an average molecular weight of about 50,000 or more is preferred. The upper limit of the molecular weight of dextran is not particularly limited, but the molecular weight is usually about 500,000 or less.

Examples of the nanoparticles used in the present invention include particles containing at least one selected from the group consisting of amino acids, amino acid derivatives, oligomers and polymers thereof, and saccharides; particles containing at least one selected from the group consisting of amino acids, amino acid derivatives, oligomers thereof, and saccharides; particles containing at least one selected from the group consisting of amino acids and saccharides; or particles containing at least one type of amino acid.

An alkyl cyanoacrylate monomer is preferable as the cyanoacrylate monomer. The number of carbon atoms in the alkyl group is preferably from 1 to 8, more preferably from 2 to 6, and further preferably from 3 to 5, and the alkyl group may be linear or branched. In addition, at least one of the carbon atoms constituting the alkyl group may be replaced by a halogen atom (chlorine, bromine, iodine). Specific examples of a preferable cyanoacrylate monomer can include methyl-2-cyanoacrylate, ethyl-2-cyanoacrylate, n-propyl-2-cyanoacrylate, i-propyl-2-cyanoacrylate, n-butyl-2-cyanoacrylate, i-butyl-2-cyanoacrylate, n-pentyl-2-cyanoacrylate, n-hexyl-2-cyanoacrylate, n-heptyl-2-cyanoacrylate, n-octyl-2-cyanoacrylate, and the like. Among those, particularly, n-butyl-2-cyanoacrylate (nBCA) represented by the following formula can preferably be used, which has been used as an adhesive for wound closure in the field of surgery.

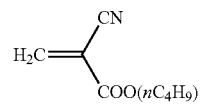

In the production process of the nanoparticles, the polymerization reaction may be allowed to proceed by dissolving at least one type of polymerization initiator/stabilizer in a suitable solvent, and then adding at least one type of cyanoacrylate monomer to the resulting solution under stirring, and keeping stirring as appropriate. Only one type of cyanoacrylate monomer may be used, or two or more types of cyanoacrylate monomers may be used.

In cases where a saccharide(s) and/or a polysorbate(s) is/are used as a polymerization initiator/stabilizer, the concentration of the saccharide and/or polysorbate (if two or more kinds of saccharides and/or polysorbates are used, the total concentration thereof) in a polymerization reaction solution at the beginning of the reaction is not particularly limited, but it is usually about 0.5% to 10%, and preferably about 0.75% to 7.5%. As used herein, the concentration of saccharides is expressed as % (w/v), and the concentration of polysorbates is expressed as % (v/v). For example, if a saccharide is used alone, the above-described respective concentration ranges indicate "0.5% (w/v) to 10% (w/v)" and "0.75% (w/v) to 7.5% (w/v)". Moreover, if 5% (w/v) of saccharide and 1% (v/v) of polysorbate are used in combination, the total concentration thereof is expressed as 6%. It should be noted that, in cases where a monosaccharide(s) (for example, glucose) is/are used alone, the monosaccharide(s) is/are preferably used at a concentration of about 2.5% (w/v) to 10% (w/v).

In cases where an amino acid-based molecule(s) is/are used as a polymerization initiator/stabilizer, the concentration of the amino acid-based molecule (if two or more kinds of amino acid-based molecules are used, the total concentration thereof) in a polymerization reaction solution at the beginning of the reaction is not particularly limited, but it is usually about 0.1% (w/v) to 3% (w/v). In cases where an amino acid-based molecule(s) is/are used in combination with a saccharide(s) and/or a polysorbate(s), the concentration of the amino acid-based molecule(s) to be used may be a concentration lower than this range of concentration.

As a solvent for the polymerization reaction, an aqueous solvent which is based on water (for example, water, aqueous solution of lower alcohol, and the like) may be used, and water is usually preferably used. Since anionic polymerization is initiated by hydroxide ions, the velocity of polymerization is influenced by the pH of the reaction solution. When the pH of the reaction solution is high, the polymerization proceeds rapidly because of a high concentration of hydroxide ions. When the pH is low, the polymerization is slowed down. A moderate velocity of polymerization can be obtained usually under acidic conditions of about pH 2 to 4, particularly under acidic conditions of about pH 1.5 to 3.0 in cases where an amino acid-based molecule is used as a polymerization initiator/stabilizer. An acid added to make the reaction solution acidic is not particularly limited, but any of inorganic and organic acids can be used. For example, hydrochloric acid can preferably be used in the production of polymer particles because hydrochloric acid does not adversely affect the reaction and it evaporates after the reaction. However, an acid that can be used is not limited to hydrochloric acid. The concentration of hydrochloric acid is not particularly limited, but it may be appropriately selected within the range from about 0.0005 N to 0.5 N.

A method called Miniemulsion (Weiss, C. K. et al., Preparatio, Macromolecules, 2007, Vol. 40, p. 928-938) is known as a method of synthesizing nano-sized polymer particles, in which cyanoacrylate monomer molecules are polymerized by means of an amino acid as a polymerization initiator. In this method, a step of preparing emulsions by using a solution of hexadecane and hydrochloric acid as a solvent and using the surfactant SDS is essential. According to the above-described method developed by the present inventor, nano-sized polymer particles can be synthesized by the polymerization reaction in an aqueous solvent, and there is therefore no need to use an organic solvent as a solvent and to use a surfactant. Moreover, in the method of the inventor, nano-sized polymer particles can also be produced by using a polymerization initiator/stabilizer other than polysorbate, and, therefore, nanoparticles that do not contain any surfactant selected from anionic surfactants, cationic surfactants, amphoteric surfactants, and non-ionic surfactants, including Tween-series surfactants, can be prepared. The effect of nano-sized polymer particles synthesized by the Miniemulsion method on fungi is unknown.

The concentration of the cyanoacrylate monomer(s) in a polymerization reaction solution at the beginning of the reaction is not particularly limited, but it is usually about 0.5% (v/v) to 2.0% (v/v), and preferably about 0.8% (v/v) to 1.2% (v/v).

The reaction temperature is not particularly limited, but the reaction is preferably carried out at room temperature because it is simple. As for the reaction time, the reaction velocity varies depending on the pH of the reaction solution, the type of the solvent, and the like, and therefore the reaction time is appropriately selected depending on these factors. The reaction time is usually, but is not particularly limited to, about 10 minutes to 5 hours, preferably about 30 minutes to 4 hours. As the obtained polymer particles are usually used as neutral particles, it is preferred to neutralize the reaction solution by adding thereto a base such as aqueous sodium hydroxide solution or the like after completion of the reaction. Particles may be recovered by filtering the reaction solution after completion of the reaction through a filter, and washing the particles with sterilized water as appropriate.

By the above-described method, nano-sized cyanoacrylate polymer particles with an average particle diameter of less than 1000 nm can be easily produced. The lower limit of the particle size is not particularly limited, but the particle diameter of particles produced by the above-described polymerization reaction is usually about 7 nm or more. The average particle diameter of the particles is preferably 20 nm to 600 nm, more preferably 50 nm to 550 nm. The size of the particles can be controlled by adjusting the concentration of cyanoacrylate monomer(s) in the reaction solution, the pH, and/or the reaction time. Moreover, in cases where at least one selected from saccharides and polysorbates is used as a polymerization initiator/stabilizer, the particle size can also be controlled by changing the concentration and/or the type of the polymerization initiator/stabilizer (see, e.g. Patent Documents 3 and 4). In general, the particle size becomes large in cases where the pH of the reaction solution is high, where the reaction is carried out for a longer time, and where the concentration of saccharide(s) in the reaction solution is lowered, whereas the particle size becomes small in cases where a polysorbate(s) is/are used as a polymerization initiator/stabilizer. Particles with a desired size can be produced by appropriately combining these reaction conditions.

The electric charge (Zeta potential) of the nanoparticles is not particularly limited, but it is usually about −50 mV to 0 mV. "Zeta potential" represents an electric charge on the surface of particles, and is an indicator of the dispersion stability of particles. The size and Zeta potential of particles may be easily measured with, for example, a commercially available device utilizing a He—Ne laser (such as Zetasizer manufactured by Malvern Inst.UK).

It is thought that, in nanoparticles produced by using an amino acid-based molecule(s) as a polymerization initiator/stabilizer, the amino acid-based molecule(s) is/are incorporated not only by adhesion to the particles, but also by a covalent linkage of a —COO group in the amino acid structure to a carbon of the terminal ethylene structure in the cyanoacrylate. By utilizing a functional group of the amino acid-based molecule covalently bound to the polymeric moiety, the nanoparticles can be immobilized onto a desired material by covalent linkage. The content rate of the amino acid-based molecule(s) in the particles obtained by the above-described method is usually about 20% to about 65%. The content rate of the amino acid-based molecule(s) can be calculated by measuring the absorbance at an appropriate wavelength of filtrates obtained when the polymerization reaction solution was filtered and washed, determining the amount of the amino acid-based molecule(s) in the filtrates (i.e., the amount of the amino acid-based molecule(s) not incorporated into the particles) based on the measured absorbance, and then calculating the content rate according to the following formulae:

Content of amino acid-based molecules=(Amount of added amino acid-based molecules)−(Amount of amino acid-based molecules in the filtrates)

Content rate of amino acid-based molecules (%)=Content of amino acid-based molecules/ Amount of added amino acid-based molecules× 100.

The antimicrobial agent according to the present invention has effects to inhibit germination of fungal spores, growth of colonies, and elongation of hyphae. Fungi targeted by the antimicrobial agent are not particularly limited, and include various types of true fungi and filamentous fungi. For example, the antimicrobial agent according to the present invention can preferably be used against true fungi that infect animals including human to cause infectious diseases and against filamentous fungi that infect plants to cause diseases. Specific examples of the target fungi include, but are not limited to, fungi belonging to the genera *Alternaria, Aspergillus, Botrytis, Cladosporium, Cryptococcus, Diaporthe, Fusarium, Magnaporthe, Paecilomyces, Penicillium*, and the like.

The nanoparticles used in the present invention do not contain an antimicrobial active ingredient effective against fungi whose growth is to be inhibited. The term "antimicrobial active ingredient" means a chemical ingredient which exerts a biochemical action on a metabolic pathway or physiological function in fungi to inhibit their growth, and specifically means a chemical ingredient which can be used for inhibition of fungal growth, including antibiotics and the like. The nanoparticles are not limited to particles that do not contain any antimicrobial active ingredient at all, and particles containing an antimicrobial active ingredient in such a tiny amount that the growth of fungi which are originally sensitive to the antimicrobial active ingredient is not successfully inhibited are also included in the nanoparticles that "do not contain an antimicrobial active ingredient effective against fungi whose growth is to be inhibited," which can be used in the present invention. By defining the concentration of an antimicrobial active ingredient contained in particles as the amount of an antimicrobial active ingredient contained in a unit volume of the particles, the phrase "such a tiny amount that the growth of fungi is not successfully inhibited" refers to such an amount of the antimicrobial active ingredient that the growth of a sensitive fungus (growth of fungal body, or elongation of hyphae) cannot be inhibited when the same concentration of the antimicrobial active ingredient as that contained in particles as defined above is allowed to directly act on the sensitive fungus without incorporating the antimicrobial active ingredient into particles. The nanoparticles used in the present invention can be particles that do not contain any antimicrobial active ingredient such as an antibiotic at all.

The detailed principle by which nano-sized cyanoacrylate polymer particles can exert their antimicrobial activity against fungi is unknown. Although the scope of the present invention is not bound by theory, the following is presented relating to the principle. It is believed that the nanoparticles specifically attach to the outer wall of fungi and the outer membrane of spores to cause focal damages on the functions of the outer wall or the outer membrane, which results in inhibition of elongation of hyphae and germination of spores.

The strength of antimicrobial activity against fungi and the antimicrobial spectrum of the nanoparticles can be controlled through the selection of the type of a polymerization initiator/stabilizer used in the synthesis of the particles (i.e., the type of a polymerization initiator/stabilizer incorporated into the particles). Aspartic acid is one example of a polymerization initiator/stabilizer that can provide a particularly broad antimicrobial spectrum. Glycine-containing nanoparticles can exert an excellent antimicrobial activity against fungi belonging to the genus *Alternaria, Aspergillus terreus*, fungi belonging to the genus *Cladosporium*, fungi belonging to the genus *Fusarium*, fungi belonging to the genus *Paecilomyces*, and *Penicillium pinophilum*. Dextran-containing nanoparticles can exert an excellent antimicrobial activity against fungi belonging to the genus *Alternaria, Aspergillus terreus*, fungi belonging to the genus *Cladosporium*, fungi belonging to the genus *Fusarium*, fungi belonging to the genus *Paecilomyces*, and fungi belonging to the genus *Penicillium*.

Additionally, examples of fungi against which the antimicrobial agent according to the present application is particularly effective include fungi belonging to the genera *Alternaria, Cladosporium, Fusarium, Paecilomyces*, and *Penicillium*. Any of the nanoparticles can exert a very high antimicrobial activity against these fungi, irrespective of the type of the polymerization initiator/stabilizer.

The antimicrobial agent according to the present invention may consist solely of the nanoparticles, or may be in the form of nanoparticles dispersed in a suitable solvent. For example, the antimicrobial agent according to the present invention can be provided in the form of lyophilized particles, or in the form of a particle suspension, in which the nanoparticles are contained at a concentration higher than a commonly used concentration or at a working concentration. When the antimicrobial agent according to the present invention is used as a medicament, it can also be further combined with known carrier ingredients such as excipient, diluent and the like for formulation into a dosage form suitable for a particular administration mode. The antimicrobial agent may contain a single type of nanoparticles alone, or may contain two or more types of nanoparticles (i.e., multiple types of nanoparticles containing different polymerization initiators/stabilizers).

If the antimicrobial agent according to the present invention is used to treat or prevent fungal infections in humans, the dose is not particularly limited, and the particles may be administered to an adult human (with a body weight of about 60 kg) usually in about 0.1 g to 10 g per dose, for example, about 0.5 g to 5 g per dose. If the antimicrobial agent according to the present invention is used in animals including fishes and the like but excluding human, it may be administered in an amount based on the above-described dosage.

Examples of a method of administering the particles include parenteral administration, such as subcutaneous, intramuscular, intraperitoneal, intraarterial, intravenous, or intrarectal administration, as well as oral administration. Specifically, the nanoparticles may be suspended in, for example, saline and then administered parenterally by injection or the like. The nanoparticles may also be administered orally as a capsule formulation, syrup formulation, or the like. In addition to systemic administration, the nanoparticles can also be applied topically in the form of a transdermal patch, ointment, or the like. If the nanoparticles are administered to livestock, poultry, or cultured fishes, the nanoparticles may be mixed with feed and then administered orally. If the particles are used for sterilization of medical devices or instruments and the like, the particles may be dispersed in, for example, water, an alcoholic solvent, or the like, and the medical devices or instruments and the like may be dipped therein. By administering the nanoparticles to living organisms or bringing the nanoparticles into contact with devices or instruments and the like, the nanoparticles are brought into contact with fungi whose growth is to be inhibited, which can result in fungal growth inhibition.

The antimicrobial agent according to the present invention is particularly useful as a control agent against plant diseases caused by filamentous fungi. The agent can be applied to plants during cultivation, or can be used for disinfection and cleaning of farm equipment and household gardening instruments which have been or might be contaminated with phytopathogenic filamentous fungi. The amount of the agent to be applied to plants can be appropriately selected depending on the extent of disease development. For example, without limitation, a particle dispersion liquid with a particle concentration of about 0.01 g to 1 g, or about 0.001% to 1%, may be applied to plants (including any part of the plant, such as root, stem, leaf, fruit, flower, etc.), ground soil, planter soil, seeding box, or the like. Seed disinfection can also be carried out by immersing seeds in a particle dispersion liquid. In the case of sterilization of farm equipment, the particles may be dispersed in water, an alcohol solvent or the like at an appropriate concentration, for example, nearly at the above-described concentration, to dip farm equipment therein or to spray farm equipment therewith. Although the strength of antimicrobial activity of the nanoparticles may also vary depending on the target fungal species, the nanoparticles can exert their antimicrobial activity when used approximately at a concentration as described above.

EXAMPLES

The present invention will now be described more concretely by way of examples. However, the present invention is not limited to the examples below.

1. Production of Nanoparticles

Amino acid-containing or dextran-containing nanoparticles were produced in accordance with the methods described in Patent Documents 8 and 9. Specific procedures are as described below.

(1) Amino Acid-Based Synthesis System

In 10 mL of 0.001 N HCl, 100 mg of amino acid was dissolved, and the pH of the solution was adjusted to pH=3 as needed by using 1 N hydrochloric acid. Aspartic acid and glycine were used as the amino acid.

(2) Dextran-Based Synthesis System

In 10 mL of 0.01 N HCl, 100 mg of dextran 60K was dissolved, and the pH of the solution was adjusted to pH=2 as needed by using 1 N hydrochloric acid.

Under individually stirring the solutions (1) and (2), 100 µL of nBCA was added thereto, and each mixture was stirred for 3 hours to allow the polymerization reaction to proceed. The reaction solution was neutralized (pH 7.8) by adding 1 N NaOH dropwise thereto, and then stirred for additional 30 minutes. The reaction solution was filtered by centrifugation through the Centriprep (YM-10) filter (MILLIPORE) at 3500 rpm for 15 minutes. Distilled water was added to the liquid which had not passed through the filter, and the resulting mixture was again subjected to the centrifugal filtration to wash polymerized particles. This centrifugal washing operation was repeated 4 times in total to obtain amino acid-containing or dextran-containing nano-sized polymer particles.

The average particle diameter and the Zeta-potential of the obtained particles were measured with a commercially available apparatus, Zetasizer (manufactured by Malvern Inst.UK). The results of the measurement are shown in Table 1.

TABLE 1

| | Rate of amino acid content (%) | Average particle diameter (nm) | Peak 1 (nm) | Peak range (nm) | Zeta-potential (-mV) |
|---|---|---|---|---|---|
| Gly-Nano | 51.6 | 131 | 133 | 33.7 | 16.6 |
| Asp-Nano | 28.5 | 139.5 | 153.8 | 49.5 | 18.9 |
| D60-Nano | — | 148.5 | 163.7 | 56.3 | 11.7 |

2. Antimicrobial Activity of Nanoparticles Against Various Types of True Fungi

The nanoparticles were studied for the antimicrobial activity against various fungi including animal pathogenic true fungi and phytopathogenic filamentous fungi. Agar media containing nanoparticles were prepared by autoclaving a composition of YPG agar medium (1% glucose, 0.5% peptone, 0.3% yeast extract, 0.1% monopotassium phosphate, 0.04% magnesium sulfate, 1.8% agar), adding thereto the nanoparticles to a desired final concentration, mixing the mixture and then dispensing the mixture to dishes.

(1) Test of the Antimicrobial Activity of the Nanoparticle Against Fungi Belonging to the Genus *Aspergillus* (Growth of Colonies)

*A. fumigatus* was cultured on YPG agar medium either with or without nanoparticles, and the growth of colonies (hyphae) was compared between these cultures. As for the nanoparticles, the Asp-containing nanoparticles were used in a final concentration of 0.005% (w/v) or 0.05% (w/v). The agar media were inoculated in the center with a certain amount of hyphae of *A. fumigatus* and incubated at 37° C., followed by measuring the diameter of the colony 24 and 48 hours later. The result is shown in FIG. 1. The hyphal elongation in *A. fumigatus* was clearly inhibited according to the concentration of the nanoparticles.

Figure 2:
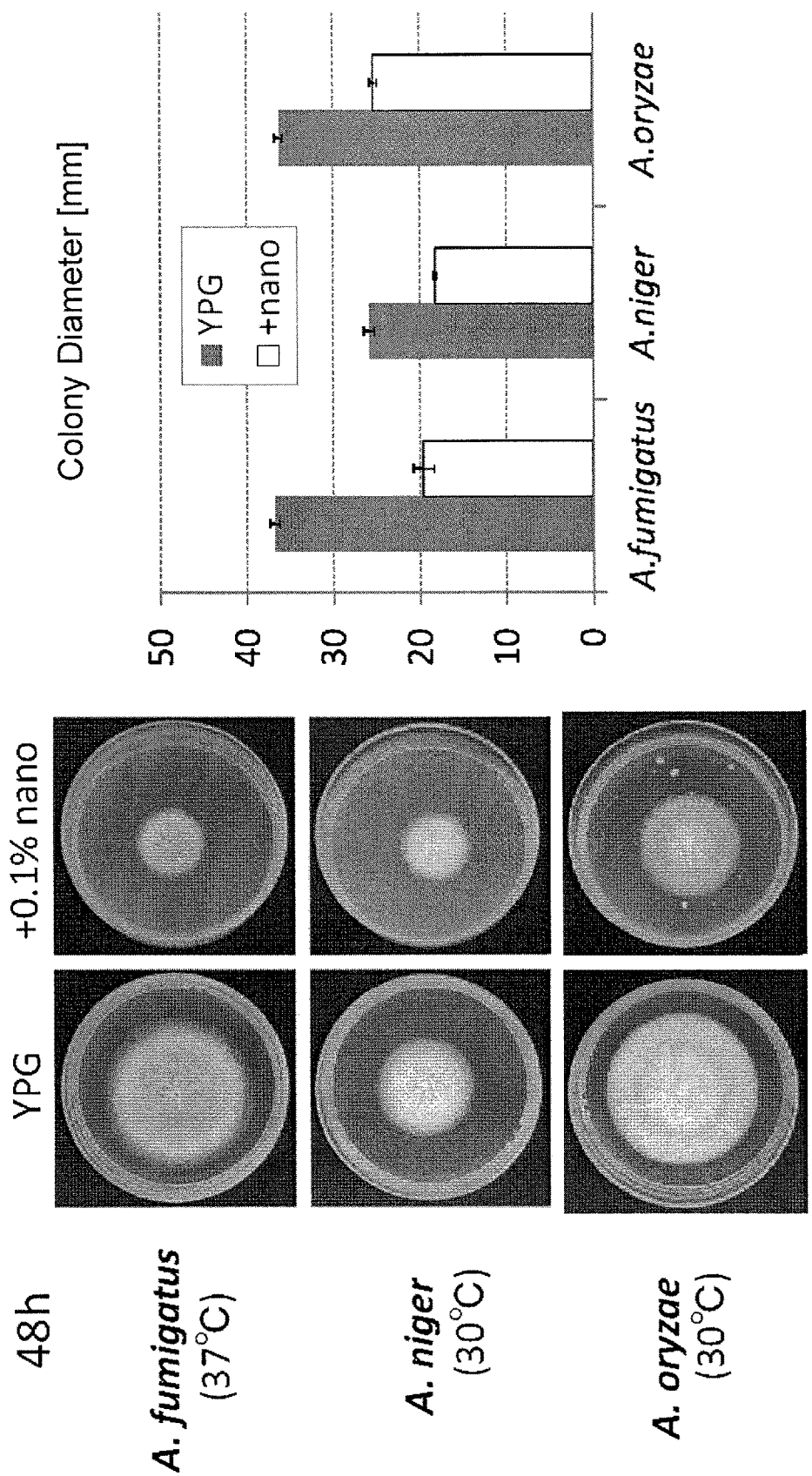

In addition to *A. fumigatus*, the effect of the nanoparticles on the growth of colonies was also similarly investigated in *A. niger* and *A. oryzae*. As for the nanoparticles, the Asp-containing nanoparticles were used in a final concentration of 0.1% (w/v). Incubation temperature for *A. niger* and *A. oryzae* was 30° C. The diameter of colonies was measured after incubation for 48 hours. The result is shown in FIG. 2. The hyphal elongation in both the fungi was clearly inhibited on the culture media supplemented with the nanoparticles.

(2) Test of the Antimicrobial Activity of the Nanoparticle Against a Fungus Belonging to the Genus *Aspergillus* (Germination of Spores)

Figure 3:
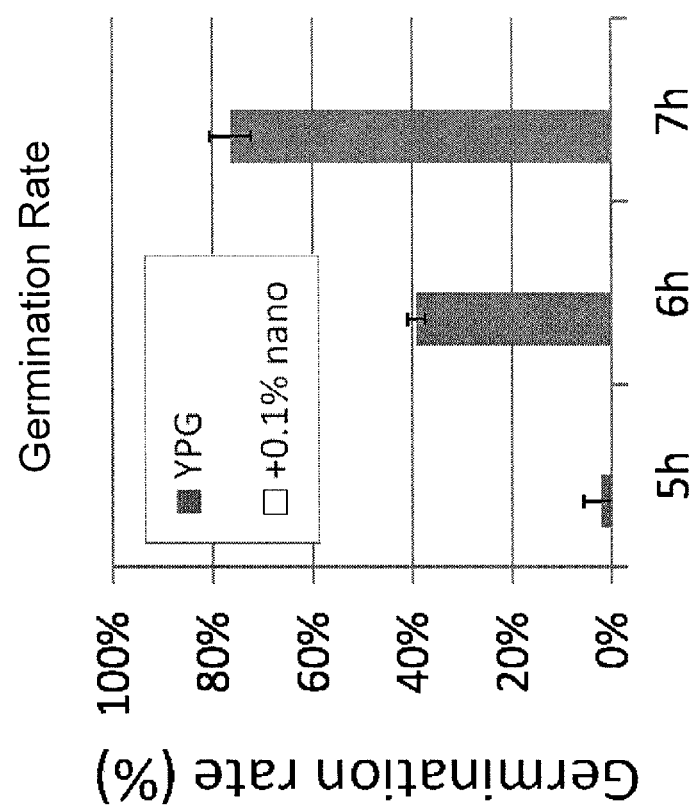

Spores of *A. fumigatus* were sprayed directly with the nanoparticles at a concentration of 0.1% (w/v), and then incubated in liquid YPG medium at 37° C. to determine the germination rate. The result indicates that, as shown in FIG. 3, germination of the spores sprayed with the nanoparticles was not observed at all even after 7 hours of incubation.

(3) Test of the Antimicrobial Activity of the Nanoparticle Against a Fungus Belonging to the Genus *Cryptococcus*

*Cryptococcus neoformans* cells were plated at a density of 100 cells per plate on YPG agar medium containing the glycine-containing nanoparticle at a concentration of 0.1% (w/v) and incubated at 30° C. for 90 hours, and then the number of colonies formed on the plates was measured.

Figure 4:
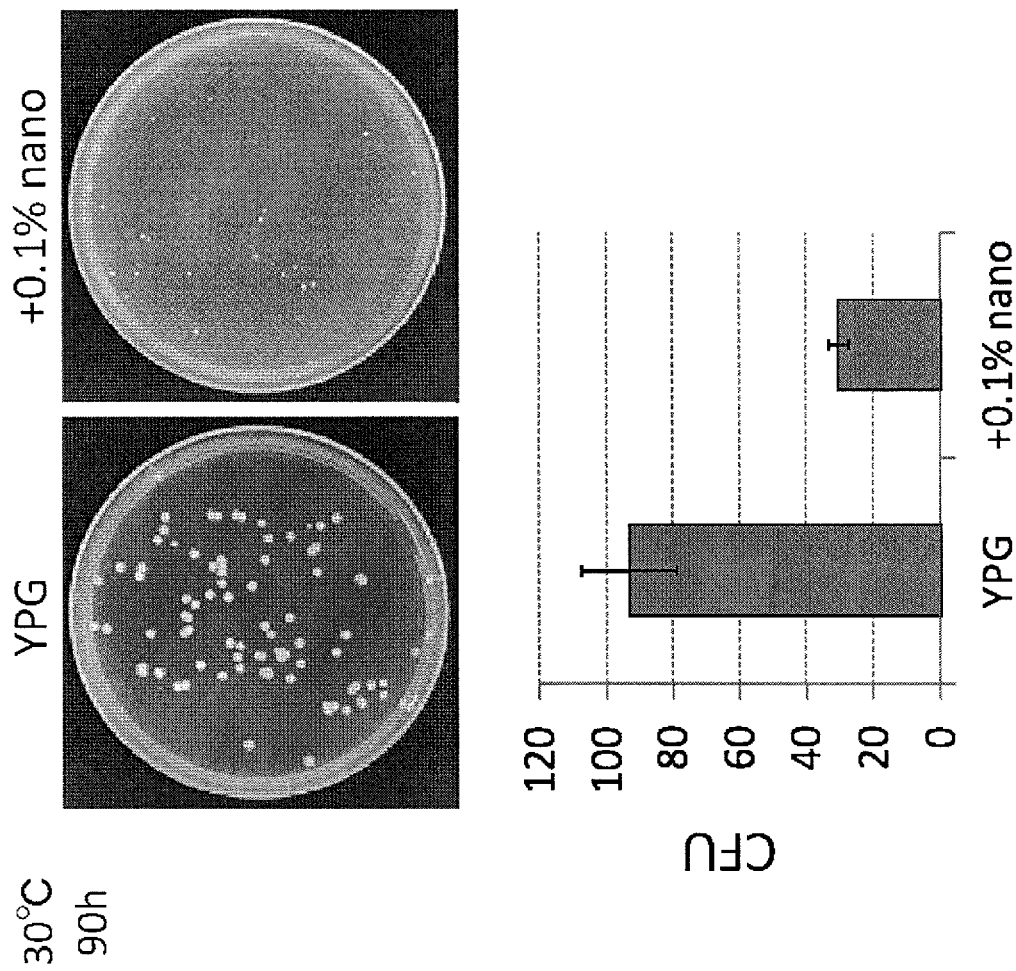

The result is shown in FIG. 4. The formation and growth of colonies was clearly inhibited on the culture media supplemented with the nanoparticles.

(4) Test of the Antimicrobial Activity of the Nanoparticle Against Various Types of Phytopathogenic Filamentous Fungi The growth of colonies on YPG agar medium containing the Asp-containing nanoparticles at a concentration of 0.1% (w/v) was investigated in various types of phytopathogenic filamentous fungi.

Test Fungi:

*Fusarium oxysporum* (the causal fungus of *Fusarium* wilt disease)

*Fusarium solani* (a pathogenic fungus for potato dry rot disease etc.)

*Magnaporthe oryzae* (the causal fungus of rice blast disease)

*Alternaria alternata* (the causal fungus of black spot disease)

*Botrytis cinerea* (the causal fungus of grey mold disease)

Figure 5:
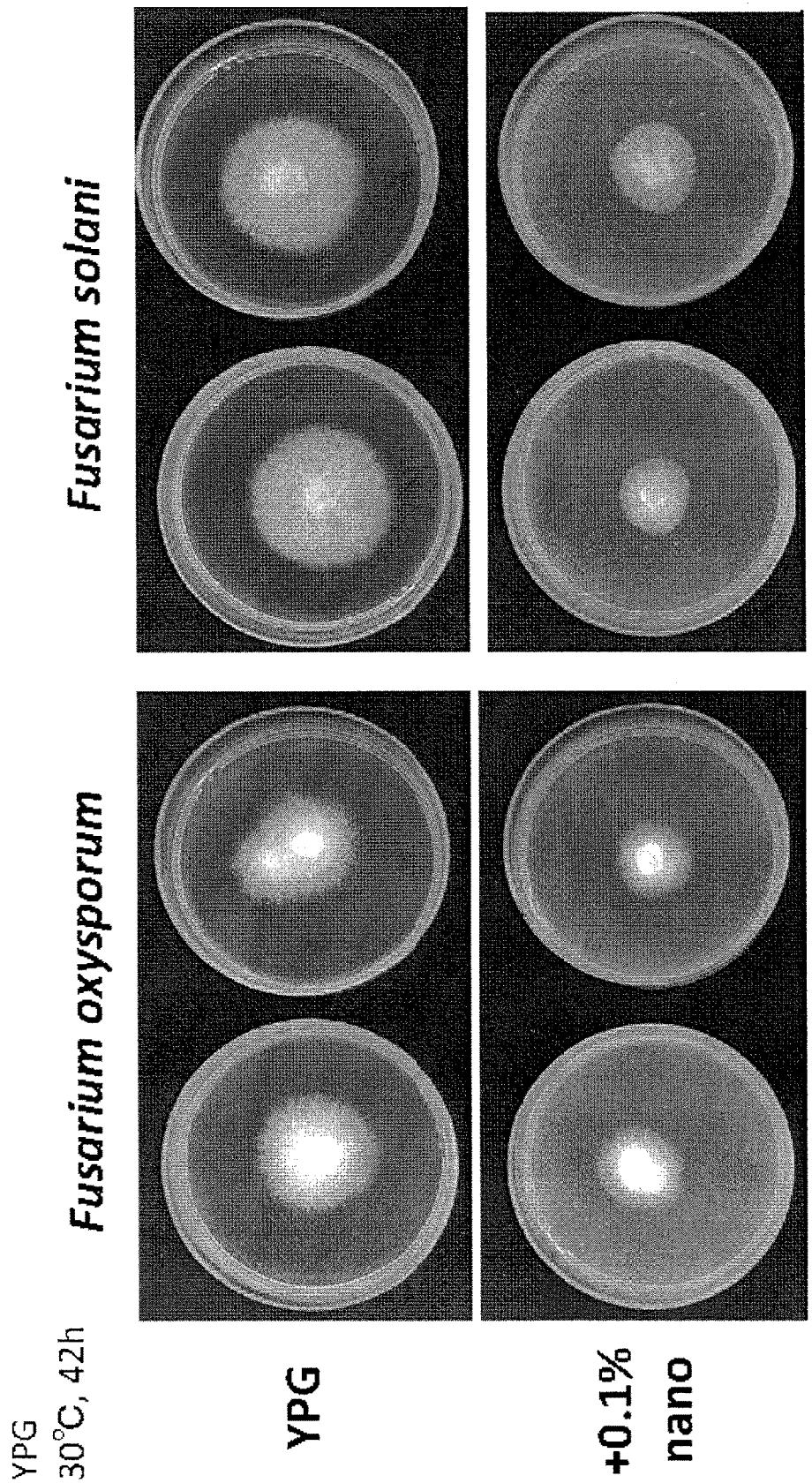
Figure 6:
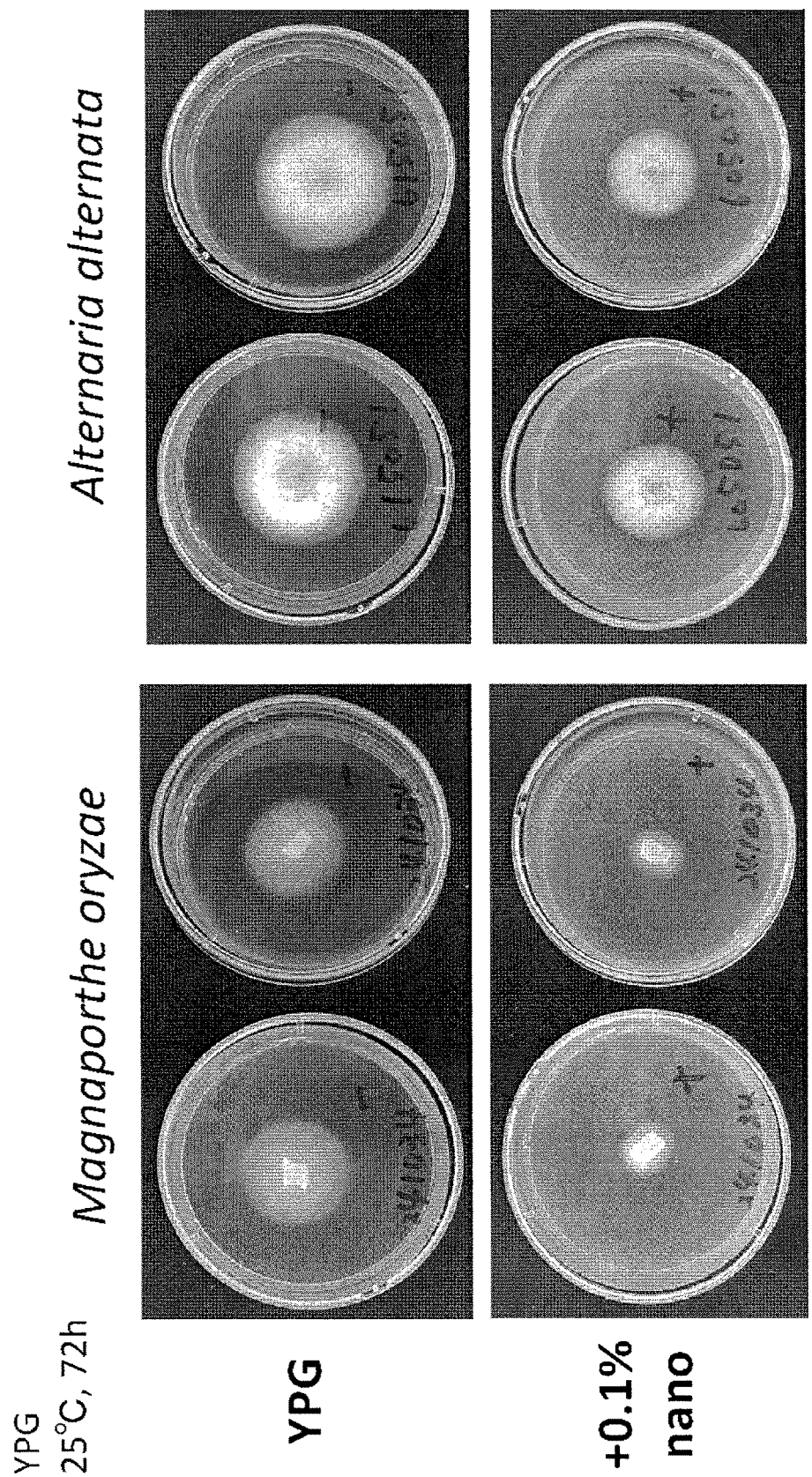
Figure 7:
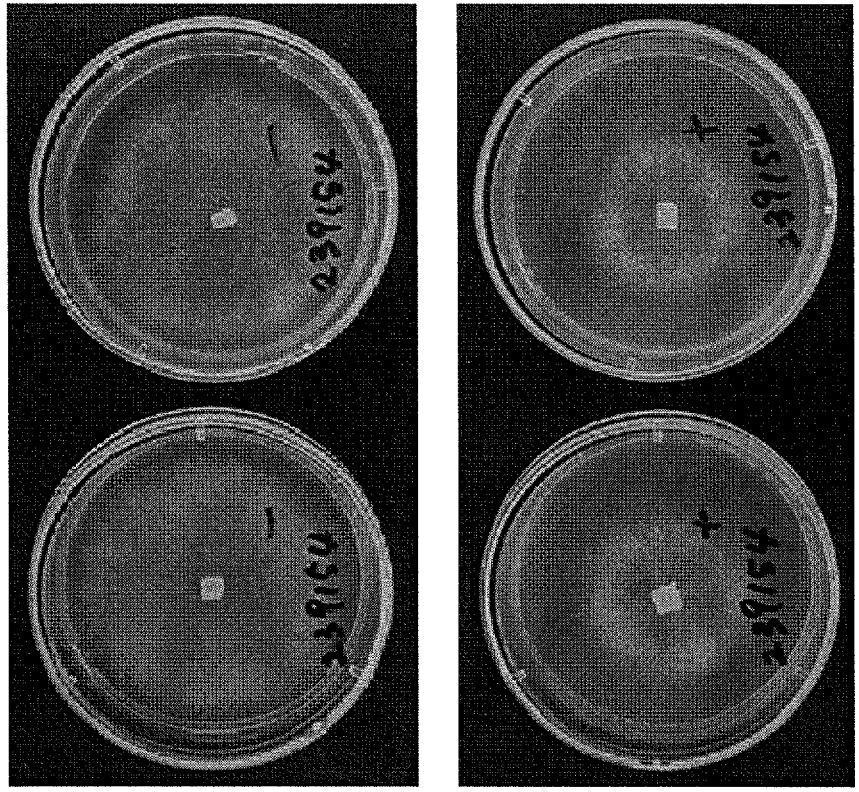

The results are shown in FIGS. 5 to 7. The hyphal elongation was clearly inhibited by the nanoparticles in any of the fungi tested.

(5) Test of the Antimicrobial Activity of the Nanoparticle Against Various Types of Fungal Strains The inhibitory effects of the nanoparticles on spore germination and hyphal elongation in various types of fungal strains stored in NBRC (the Biological Resource Center, NITE) were investigated by the procedure below.

An agar medium containing the nanoparticles at a concentration of 10 to 12 mg/ml was prepared and taken as a 1-fold dilution plate, and 2- to 2048-fold dilution plates were also prepared by serial dilution, to obtain a series of agar media containing the nanoparticles at 12 different concentrations. For the inhibitory effect on spore germination, 100 spores from each fungal strain were plated on each of the plates, incubated for a predetermined time period, and then examined for the presence or absence of spore germination. For the inhibitory effect on hyphal elongation, an appropriate volume (5 or 10 µl) of each spore suspension was spotted onto each of the culture media and incubated at 25° C. Germination and hyphal elongation on an agar medium containing no nanoparticles were measured as a control and the results were categorized into the untreated group (100%). The inhibitory effect of the nanoparticles on hyphal elongation was determined by comparing the hyphal elongation on the media containing the nanoparticles with that in the control. The result is shown in Table 2 below.

TABLE 2

| Species | NBRC No. | Asp-Nano | Gly-Nano | D60-Nano |
|---|---|---|---|---|
| Alternaria alternata | 31805 | ○ (0.2) | ● | ● |
| Aspergillus niger | 9455 | ○ (0.05) | x | x |
| Aspergillus oryzae | 105650 | ○ (0.1) | x | x |
| Aspergillus terreus | 6346 | ○ (0.7) | ● | ● |
| Cladosporium cladosporioides | 105947 | ○ (0.1) | ● | ● |
| Fusarium oxysporum | 31631 | ○ (0.7) | ○ (9.6) | ○ (4.2) |
| Paecilomyces variotii | 30539 | ○ (0.5) | ○ (4.8) | ● |
| Paecilomyces variotii | 33284 | ○ (0.5) | ● | ● |
| Penicillium pinophilum | 33285 | ○ (0.1) | ○ (0.7) | ○ (9.0) |
| Penicillium funiculosum | 100958 | ○ (0.1) | x | ○ (4.2) |

Figure 8:
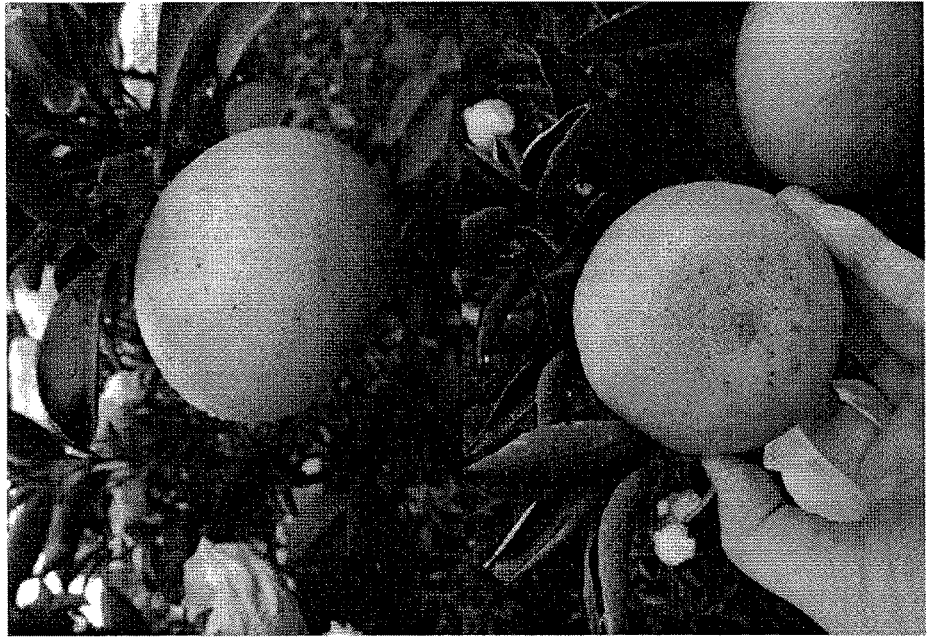
Figure 8:

○ represents a positive inhibitory effect on spore germination, while ● represents a positive inhibitory effect on hyphal elongation.
The values within the parentheses indicate the minimum concentrations (mg/mL) required to inhibit spore germination.
Asp-Nano: Asp-containing nanoparticles, Gly-Nano: Gly-containing nanoparticles, D60-Nano: dextran-containing nanoparticles (6) Control Effect Against Diseases Caused by Filamentous Fungi in Farm Field Citrus black spot disease is a disease caused by a filamentous fungus *Diaporthe citri*. In a field where a citrus variety "Setoka" was grown, an Asp-nanoparticle colloid solution in water at a concentration of 0.01% (w/v) was sprayed eight times in total with an interval of 10 days on immature fruits during the early stage of the fruit growth period after the flowering period, and the presence or absence of black spot disease development on the fruits was examined. One month after the spray application of the nanoparticles, the development of black spot disease was observed in an untreated plot but not in the nanoparticle-treated plot. Six months after the spray application of the nanoparticle, a part of fruits exhibited the development of black spot disease in a plot where a conventional antifungal spreading agent was sprayed, but the development of black spot disease was not at all observed in the nanoparticle-treated plot (FIG. 8). In addition, the nanoparticle did not adversely affect the growth of the citrus fruits, whereby citrus fruits with high quality were successfully obtained.

Carbamate pesticides have been conventionally used to control black spot disease. Although carbamate pesticides exert powerful control effects on black spot disease, they also adversely affect citruses, which may result in reduction of fruit quality. On the other hand, by means of the nanoparticles according to the present invention, citruses are protected from black spot disease, as well as the growth of citrus fruits is not adversely affected, which may result in production of citrus fruits with keeping their quality high.

The invention claimed is:

1. A method for inhibiting growth of phytopathogenic filamentous fungi, comprising bringing phytopathogenic filamentous fungi into contact with an antimicrobial agent against fungi, said agent comprising, as an effective ingredient, cyanoacrylate polymer particles having an average particle diameter of less than 1000 nm, which particles contain at least one selected from the group consisting of aspartic acid, glycine and dextran, wherein the antimicrobial agent against fungi comprises no other antifungal active ingredient.

2. The method according to claim 1, wherein the particles contain aspartic acid.

3. The method according to claim 1, wherein the cyanoacrylate is n-butyl-cyanoacrylate.

4. The method according to claim 1, wherein the phytopathogenic filamentous fungi are at least one selected from the group consisting of fungi belonging to the genera *Alternaria*, *Botrytis*, *Diaporthe*, *Fusarium*, and *Magnaporthe*.

5. A method for control of plant diseases caused by phytopathogenic filamentous fungi, comprising bringing a plant body, ground soil, planter soil, seedling box, plant seed, farm equipment, or a household gardening instrument into contact with an antimicrobial agent against fungi, said agent comprising as an effective ingredient cyanoacrylate polymer particles having an average particle diameter of less than 1000 nm, which particles contain at least one selected from the group consisting of aspartic acid, glycine and dextran, wherein the antimicrobial agent against fungi comprises no other antifungal active ingredient.

6. The method according to claim 5, wherein the cyanoacrylate polymer particles contain aspartic acid.

7. The method according to claim 5, wherein the cyanoacrylate is n-butyl-cyanoacrylate.

8. The method according to claim 5, wherein the phytopathogenic filamentous fungi are at least one selected from the group consisting of fungi belonging to the genera *Alternaria*, *Botrytis*, *Diaporthe*, *Fusarium*, and *Magnaporthe*.

9. A method for inhibiting growth of fungi, comprising bringing fungi into contact with an antimicrobial agent against fungi comprising as an effective ingredient cyanoacrylate polymer particles having an average particle diameter of less than 1000 nm, which particles contain at least one selected from the group consisting of aspartic acid, glycine and dextran, wherein the antimicrobial agent against fungi comprises no other antifungal active ingredient, and wherein the fungi are at least one true fungi or filamentous fungi selected from the group consisting of fungi belonging to *Alternaria*, *Aspergillus*, *Botrytis*, *Cladosporium*, *Cryptococcus*, *Diaporthe*, *Fusarium*, *Magnaporthe*, *Paecilomyces*, and *Penicillium*.

10. The method according to claim 9, wherein the cyanoacrylate polymer particles contain aspartic acid.

11. The method according to claim 9, wherein the cyanoacrylate is n-butyl-cyanoacrylate.

\* \* \* \* \*